United States Patent
Liu et al.

(10) Patent No.: US 10,632,081 B2
(45) Date of Patent: Apr. 28, 2020

(54) INTRALYMPHATIC DELIVERY OF HYALURONAN NANOPARTICLE FOR CANCER METASTASIS

(71) Applicant: INDUSTRIAL TECHNOLOGY RESEARCH INSTITUTE, Hsinchu (TW)

(72) Inventors: Chih-Peng Liu, Hsinchu (TW); Ya-Chin Lo, Taichung (TW); Ming-Cheng Wei, Taoyuan (TW); Maggie Lu, Zhudong Township, Hsinchu County (TW); Shuen-Hsiang Chou, Zhunan Township, Miaoli County (TW); Shih-Ta Chen, New Taipei (TW); Hsiang-Wen Tseng, New Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 616 days.

(21) Appl. No.: 15/142,170

(22) Filed: Apr. 29, 2016

(65) Prior Publication Data
US 2016/0361268 A1 Dec. 15, 2016

Related U.S. Application Data

(60) Provisional application No. 62/173,491, filed on Jun. 10, 2015.

(51) Int. Cl.
*A61K 33/24* (2019.01)
*A61K 9/51* (2006.01)
*A61K 9/00* (2006.01)
*A61K 31/555* (2006.01)

(52) U.S. Cl.
CPC .......... *A61K 9/5161* (2013.01); *A61K 9/0019* (2013.01); *A61K 31/555* (2013.01); *A61K 33/24* (2013.01)

(58) Field of Classification Search
CPC .... A61K 9/5161; A61K 33/24; A61K 9/0019; A61K 31/282
See application file for complete search history.

(56) References Cited

U.S. PATENT DOCUMENTS

| 5,582,172 | A | 12/1996 | Papisov et al. |
| 7,060,689 | B2 | 6/2006 | Goins et al. |
| 8,088,412 | B2 | 1/2012 | Forrest et al. |
| 8,895,069 | B2 | 11/2014 | Hahn et al. |
| 9,023,386 | B2 | 5/2015 | Benita et al. |
| 9,216,082 | B2 | 12/2015 | Von Segesser et al. |
| 2009/0011009 | A1 | 1/2009 | Benita et al. |
| 2009/0191152 | A1 | 7/2009 | Forrest et al. |
| 2012/0100218 | A1* | 4/2012 | Forrest ............... A61K 33/24 424/489 |
| 2014/0186415 | A1* | 7/2014 | Shih ............ A61K 47/48176 424/422 |
| 2015/0118322 | A1* | 4/2015 | Lo ................. A61K 31/4745 424/649 |

FOREIGN PATENT DOCUMENTS

| CN | 102240265 A | 11/2011 |
| CN | 102516391 A | 6/2012 |
| CN | 104548109 A | 6/2012 |
| TW | 201515661 A | 5/2015 |
| TW | I482634 B | 5/2015 |
| WO | WO 98/58649 A1 | 12/1998 |

OTHER PUBLICATIONS

Wu et al (J.Mater.Sci: Mater Med, 2012, 23:1921-1929).*
Pitarresi et al (Macromolecules An Indian Journal, Aug. 2007, vol. 3, issue 2, pp. 53-56).*
Cai et al., "Carrier-based intralymphatic cisplatin chemotherapy for the treatment of metastatic squamous cell carcinoma of the head & neck", NIH Public Access, Therapeutic Delivery, vol. 1, No. 2, Aug. 1, 2010, pp. 237-245.
Cai et al., "Intralymphatic Chemotherapy Using a Hyaluronan—Cisplatin Conjugate", Journal of Surgical Research, vol. 147, 2008, pp. 247-252.
Cai et al., "Pharmacokinetics and Disposition of a Localized Lymphatic Polymeric Hyaluronan Conjugate of Cisplatin in Rodents", Journal of Pharmaceutical Sciences, vol. 99, No. 6, Jun. 2010, pp. 2664-2671.
Cohen et al., "A novel intralymphatic nanocarrier delivery system for cisplatin therapy in breast cancer with improved tumor efficacy and lower systemic toxicity in vivo", The American Journal of Surgery, vol. 198, 2009, pp. 781-786.
Laakkonen et al., "A tumor-homing peptide with a targeting specificity related to lymphatic vessels", Nature Medicine, vol. 8, No. 7, Jul. 2002, pp. 751-755.
Liu et al., "A novel trans-lymphatic drug delivery system: Implantable gelatin sponge impregnated with PLGA—paclitaxel microspheres", Biomaterials, vol. 28, 2007, pp. 3236-3244.

(Continued)

*Primary Examiner* — Sudhakar Katakam
(74) *Attorney, Agent, or Firm* — Birch, Stewart, Kolasch & Birch, LLP

(57) ABSTRACT

Disclosed is an intralymphatic delivery method for treating lymphatic cancer using hyaluronan nanoparticles. These nanoparticles include a hyaluronic acid derivative and a platinum compound. The hyaluronan derivative includes hyaluronic acid, modified histidine and optionally one or more of a polymer or a $C_4$-$C_{20}$ alkyl. The hyaluronic acid derivative may include linking group(s) that connect the polymer or the $C_4$-$C_{20}$ alkyl to the hyaluronic acid. The platinum compound includes dichloro(1,2-diaminocyclohexane) platinum (DACHPt), cisplatin and oxaliplatin. This intralymphatic delivery method offers significant advantages for the use of platinum medicines in treating lymphatic cancer.

21 Claims, 12 Drawing Sheets

(56) References Cited

OTHER PUBLICATIONS

Liu et al., "Targeting colloidal particulates to thoracic lymph nodes", Lung Cancer, vol. 51, 2006, pp. 377-386.

Liu et al., "Translymphatic Chemotherapy by Intrapleural Placement of Gelatin Sponge Containing Biodegradable Paclitaxel Colloids Controls Lymphatic Metastasis in Lung Cancer", Cancer Research, vol. 69, No. 3, Feb. 1, 2009, pp. 1174-1181.

Luo et al., "LyP-1-conjugated nanoparticles for targeting drug delivery to lymphatic metastatic tumors", International Journal of Pharmaceutics, vol. 385, 2010, pp. 150-156.

Medina et al., "Avidin/Biotin-Liposome System Injected in the Pleural Space for Drug Delivery to Mediastinal Lymph Nodes", Journal of Pharmaceutical Sciences, vol. 93, No. 10, Oct. 2004, pp. 2595-2608.

Medina et al., "Mediastinal Node and Diaphragmatic Targeting after Intracavitary Injection of Avidin/$^{99m}$Tc-Blue-Biotin-Liposome System", Journal of Pharmaceutical Sciences, vol. 95, No. 1, Jan. 2006, pp. 207-224.

Phillips et al., "Novel Method of Greatly Enhanced Delivery of Liposomes to Lymph Nodes", The Journal of Pharmacology and Experimental Therapeutics, vol. 295, No. 1, Jun. 12, 2000, pp. 309-313.

Yan et al., "LyP-1-conjugated doxorubicin-loaded liposomes suppress lymphatic metastasis by inhibiting lymph node metastases and destroying tumor lymphatics", Nanotechnology, vol. 22, 2011, pp. 1-8.

Yan et al., "LyP-1-conjugated PEGylated liposomes: A carrier system for targeted therapy of lymphatic metastatic tumor", Journal of Controlled Release, vol. 157, 2012, pp. 118-125.

Zavaleta et al., "Use of avidin/biotin-liposome system for enhanced peritoneal drug delivery in an ovarian cancer model", International Journal of Pharmaceutics, vol. 337, 2007, pp. 316-328.

Zhang et al., "Recent advances in lymphatic targeted drug delivery system for tumor metastasis", Cancer Biology and Medicine, vol. 11, No. 4, Dec. 2014, pp. 247-254.

\* cited by examiner

INTRALYMPHATIC DELIVERY OF HYALURONAN NANOPARTICLE FOR CANCER METASTASIS

CROSS REFERENCE TO RELATED APPLICATION

This non-provisional application claims the benefit under 35 U.S.C. § 119(e) to U.S. Provisional Application No. 62/173,491, filed on Jun. 10, 2015, all of which is hereby expressly incorporated by reference into the present application. This application also expressly incorporates the disclosure of U.S. application Ser. No. 14/514,137, filed on Oct. 14, 2014, which published as US 2015/0118322 A1 on Apr. 30, 2015, into the present application.

TECHNICAL FIELD

Disclosed is a method of treating lymphatic cancer using hyaluronan nanoparticles. These nanoparticles are comprised of a hyaluronic acid derivative and a platinum compound. The hyaluronic acid derivative may include hyaluronic acid, modified histidine and optionally a polymer or a $C_4$-$C_{20}$ alkyl. The hyaluronic acid derivative may include linking group(s) that connect the polymer or the $C_4$-$C_{20}$ alkyl to the hyaluronic acid. The platinum compound may include dichloro(1,2-diaminocyclohexane) platinum (DACHPt), cisplatin and oxaliplatin.

BACKGROUND

Many metastatic tumors initially spread through lymphatic tissue and eventually form rapidly developing lymphatic tumors. Treatment of lymphatic metastatic tumors remains a great challenge given the limitations of surgical resection and the low effectiveness of radiotherapy and chemotherapy (Zhang, X., Lu, W. "Recent advances in lymphatic targeted drug delivery system", *Cancer Biol. Med.*, 2014: 247-254).

Therapies for lymphatic targeted therapy may passively or actively target the lymphatic system. An example of passive delivery is intrapleural placement of a gelatin sponge infused with an antitumor agent (Liu, J. et al. "A novel trans-lymphatic drug delivery system: Implantable gelatin sponge impregnated with PLGA—paclitaxel microspheres", *Biomaterials*, 2007: 3236-3244; Liu, J. et al. "Translymphatic Chemotherapy by Intrapleural Placement of Gelatin Sponge Containing Biodegradable Paclitaxel Colloids Controls Lymphatic Metastasis in Lung Cancer", *Cancer Res.*, 2009: 1174-1181). Nano drug delivery carriers that actively target the lymphatic system include liposomes, nanoparticles, macromolecule polymers, polymer micelles, activated carbons, silicon and nano-emulsions (Zhang, X., Lu, W. "Recent advances in lymphatic targeted drug delivery system", *Cancer Biol. Med.*, 2014: 247-254). LyP-1 conjugated nanocarriers, and hyaluronic acid nanocarriers are specific developments in lymphatic targeting drug delivery systems.

LyP-1 (CGNKRTRGC) is a cyclic nonapeptide that specifically recognizes the p32/gC1q receptor, which is overexpressed in lymphatic tumors (Laakkonen, P. et al. "A tumor-homing peptide with a targeting specificity related to lymphatic vessels", *Nat. Med.*, 2002: 751-755). Yan et al. conjugated Lyp-1 to liposomes containing doxorubicin and treated lymphatic tumors (Yan, Z. et al. "LyP-1-conjugated doxorubicin-loaded liposomes suppress lymphatic metastasis by inhibiting lymph node metastases and destroying tumor lymphatics", *Nanotech.*, 2011: 1-8; Yan, Z. et al. "LyP-1-conjugated PEGylated liposomes: A carrier system for targeted therapy of lymphatic metastatic tumor", *J. Control. Release*, 2012: 118-125). Luo et al. conjugated Lyp-1 to PEG-PLGA nanoparticles to target lymphatic tumors (Luo, G. et al. "LyP-1-conjugated nanoparticles for targeting drug delivery to lymphatic metastatic tumors", *Pharm. Nanotech.*, 2010: 150-156).

Hyaluronic acid (HA) is a natural polysaccharide of alternating D-glucuronic acid and N-acetyl D-glucosamine that is distributed into the lymphatic system and is a ligand for the CD44 receptor, which is overexpressed in lymphatic tumors (Cai, S. et al. "Pharmacokinetics and Disposition of a Localized Lymphatic Polymeric Hyaluronan Conjugate of Cisplatin in Rodents", *J. Pharm. Sci.*, 2010: 2664-2671). Cai et al. complexed cisplatin to native hyaluronic acid and treated lymphatic tumors (Cai, S. et al. "Intralymphatic Chemotherapy Using a Hyaluronan-Cisplatin Conjugate", *J. Surgical. Res.*, 2008: 247-252; Cohen, M. et al. "A novel intralymphatic nanocarrier delivery system for cisplatin therapy in breast cancer with improved tumor efficacy and lower systemic toxicity in vivo", *Am. J. Surg.*, 2009: 781-786; Cai, S. et al. "Carrier-based intralymphatic cisplatin chemotherapy for the treatment of metastatic squamous cell carcinoma of the head & neck", *Ther. Delia*, 2010: 237-245; Cai, S. et al. "Pharmacokinetics and Disposition of a Localized Lymphatic Polymeric Hyaluronan Conjugate of Cisplatin in Rodents", *J. Pharm. Sci.*, 2010: 2664-2671; Forrest, L. et al. Intralymphatic Chemotherapy Drug Carriers, U.S. Pat. No. 8,088,412 B2, Jan. 3, 2012). In an alternative application of hyaluronic acid that does not target the lymphatic system, Hahn et al. treated non-lymphatic tumors with a doxorubicin or epirubicin loaded micelle of an anti-Flt1 peptide (GNQWFI, KGNQWFI or GGNQWFI) conjugated to native hyaluronic acid, where the anti-Flt1 peptide targeted VEGF (Hahn, S. et al. Drug Delivery System Using Hyaluronic Acid-Peptide Conjugate, U.S. Pat. No. 8,895,069 B2, Nov. 25, 2014).

SUMMARY

Disclosed is a method of treating lymphatic cancer using hyaluronan nanoparticles. The hyaluronan nanoparticles may comprise a hyaluronic acid derivative and a platinum compound. The hyaluronic acid derivative itself may comprise: a hyaluronic acid; a modified histidine; optionally a polymer or $C_4$-$C_{20}$ alkyl; and optionally linking group(s) between the polymer or $C_4$-$C_{20}$ alkyl and hyaluronic acid, wherein the modified histidine and the optional polymer or $C_4$-$C_{20}$ alkyl, if present, are grafted to at least one primary hydroxyl group of the hyaluronic acid to allow the hyaluronic acid to form a hyaluronic acid derivative. One embodiment includes a graft ratio of the modified histidine is within 1-100% based on the total number of hydroxyl groups on the hyaluronic acid, and a graft ratio of the optional polymer or $C_4$-$C_{20}$ alkyl is within 0-40% based on the total number of hydroxyl groups on the hyaluronic acid. In another embodiment, the platinum compound may comprise, but is not limited to, one or more of dichloro(1,2-diaminocyclohexane) platinum (DACHPt), cisplatin and oxaliplatin.

DETAILED DESCRIPTION

Figure 1:
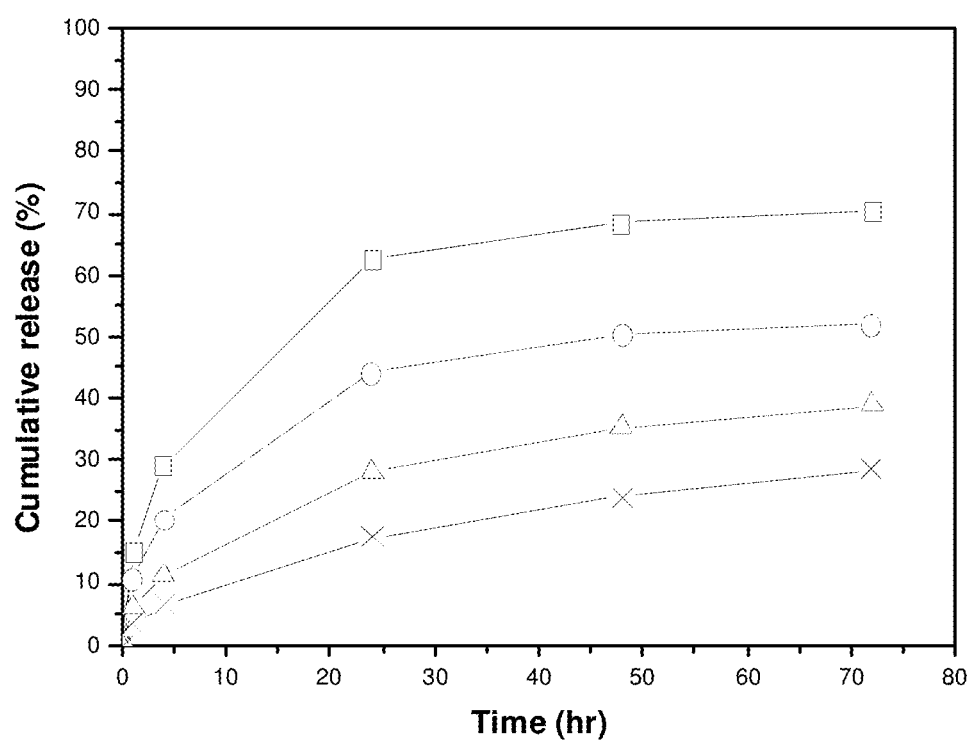
FIG. 1. shows in vitro release profiles of platinum from various BocHis grafted HA-based nanoparticles in phosphate buffered saline (pH 7.4) at 37° C. (Square-0% BocHis (PtHC16001), Circle-17% BocHis, Triangle-40% BocHis (PtHC604), X-70% BocHis).

In the following detailed description, for purposes of explanation, numerous specific details are set forth in order to provide a thorough understanding of the disclosed embodiments. It will be apparent, however, that one or more embodiments may be practiced without these specific details. In other instances, illustrative structures and devices are schematically shown.

In one embodiment of the present disclosure, the present disclosure provides a method of treating tumors in the lymphatic system of a subject with hyaluronan nanoparticle containing a hyaluronic acid derivative and a platinum compound. Native hyaluronic acid is presented in Formula (I) below.

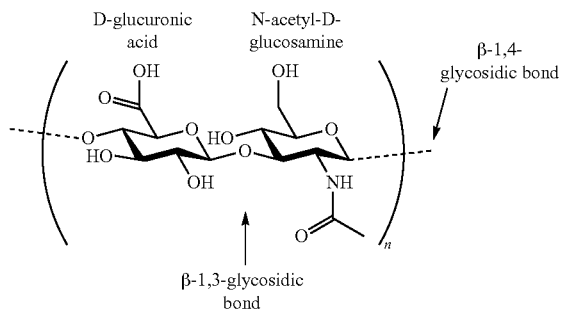

Formula I

In one embodiment, the hyaluronic acid derivative may comprise, but is not limited to, a hyaluronic acid, a modified histidine, and optionally a polymer or $C_4$-$C_{20}$ alkyl. In one embodiment, the modified histidine and optionally the polymer or $C_4$-$C_{20}$ alkyl are grafted to at least one primary hydroxyl group of the hyaluronic acid, optionally through a linking group. In such an embodiment, the modified histidine, the polymer or $C_4$-$C_{20}$ alkyl and the hyaluronic acid form a hyaluronic acid derivative.

In one embodiment, in the hyaluronic acid derivative of the present disclosure, a molecular weight of the hyaluronic acid is about 7,000-1,500,000 Daltons. In another embodiment, in a biomedical composition of the present disclosure, a molecular weight of the hyaluronic acid is about 7,000-350,000 Daltons. In other embodiments, the molecular weight of the hyaluronic acid may be about 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,0000, 26,000, 27,000, 28,000, 29,000, 30,000, 31,000 or 32,000 Daltons.

In another embodiment, a molecular weight of the hyaluronic acid derivative formed by the modified histidine and the hyaluronic acid, or formed by the modified histidine, the optional polymer or $C_4$-$C_{20}$ alkyl and the hyaluronic acid may be about 7,000-1,500,000 Daltons. In another embodiment, a molecular weight of the preceding hyaluronic acid derivative may be about 7,000-1,200,000 Daltons. In yet another embodiment, a molecular weight of the preceding hyaluronic acid derivative may be about 7,000-600,000 Daltons.

In one embodiment of the hyaluronic acid derivative of the present disclosure, examples for suitable modified histidine may comprise, for example, Boc-histidine, Cbz-histidine, Fmoc-histidine, Ac-histidine, or Trt-histidine, etc., but is not limited thereto. In a general embodiment, the alpha-nitrogen of histidine may be protected by an acyl derivative. In another embodiment, the modified histidine may form an ester with a hydroxyl on the hyaluronic acid. In yet another embodiment the imidazole on the histidine may be unprotected.

In addition, in one embodiment, the graft ratio of the modified histidine may be about 1%, 5%, 10%, 20%, 30%, 40%, 50%, 60%, 70%, 80%, 90% or 100% based upon the total number of hydroxyl groups on the hyaluronic acid.

Furthermore, in the hyaluronic acid derivative, in another embodiment, illustrative examples for suitable the polymer component include one or more of polyethylene glycol (PEG), polycaprolactone (PCL), poly lactic acid (PLA), polyglycolic acid (PGA), poly(lactic-co-glycolic acid) (PLGA) or polyvinylpyrrolidone (PVP), etc., but is not limited thereto. In another embodiment the polymer may be polyethylene glycol (PEG).

In addition, in one embodiment, in the hyaluronic acid derivative, the molecular weight of the preceding polymer may be about 300-10,000 Daltons. In another embodiment, the molecular weight of the polymer may be about 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700 or 3,800 Daltons.

Moreover, in the hyaluronic acid derivative of the present disclosure, examples for the $C_4$-$C_{20}$ alkyl may comprise, but are not limited to, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, etc.

In addition, in one embodiment, the graft ratio of the optional polymer or $C_4$-$C_{20}$ alkyl may be about 0%, 1%, 5%, 10%, 15%, 20%, 25%, 30%, 35% or 40% based upon the total hydroxyl groups on the hyaluronic acid.

In another embodiment, a graft ratio of the modified histidine to the hyaluronic acid may be within 1-100%, however, it is noted that a graft ratio of the optional polymer or $C_4$-$C_{20}$ alkyl to the hyaluronic acid is within 0-40% based upon the total hydroxyl groups on hyaluronic acid. Therefore, in one embodiment, it is understood that the hyaluronic acid derivative may have or may not have the optional polymer or $C_4$-$C_{20}$ alkyl grafted thereto. In other words, the hyaluronic acid derivative of the present disclosure optionally comprises the polymer or $C_4$-$C_{20}$ alkyl.

In one embodiment, a graft ratio of the modified histidine may be within 1-100% based on the total number of hydroxyl groups on the hyaluronic acid, while a graft ratio of the optional polymer or $C_4$-$C_{20}$ alkyl is 0, that is, the hyaluronic acid derivative does not have the optional polymer or $C_4$-$C_{20}$ alkyl grafted thereto. In one embodiment, an exemplificative formula for the hyaluronic acid derivative may be shown as the following Formula (II), but it is not limited thereto:

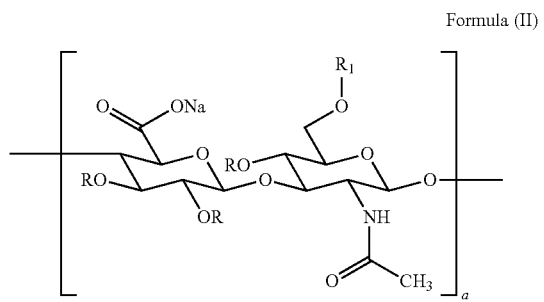

Formula (II)

In Formula (II), $R_1$ may be the modified histidine, R may be the modified histidine or H, and a may be a positive integer of 5-2000, but it is not limited thereto. A sodium carboxylate salt is one embodiment, but alternative embodiments may include other Group IA elements, such as potassium.

In other embodiments, the hyaluronic acid derivative has the optional polymer or $C_4$-$C_{20}$ alkyl grafted thereto, and in this embodiment, a graft ratio of the modified histidine may be within 1-99% based on the total number of hydroxyl groups on the hyaluronic acid, while a graft ratio of the polymer or $C_4$-$C_{20}$ alkyl is within 1-40%. In one embodiment, an exemplificative formula for the hyaluronic acid derivative may be shown as the following Formula (III), but is not limited thereto:

In the Formula (III), $R_1$ may be the modified histidine, and $R_2$ may be the polymer or $C_4$-$C_{20}$ alkyl, optionally connected via linking group(s), and R may be the modified histidine, polymer, $C_4$-$C_{20}$ alkyl or H. In addition, p and q are positive integers, and a ratio of p to q may be between 0.1-100, but is not limited thereto. In one embodiment, a ratio of p to q may be between 0.1-20. A sodium carboxylate salt is one embodiment, but alternative embodiments may include other Group IA elements such as potassium.

In one embodiment, the at least one primary hydroxyl group of the hyaluronic acid may comprise a hydroxyl group located on the fifth carbon atom of a N-acetyl-D-glucosamine of at least one disaccharide unit of the hyaluronic acid, but is not limited thereto.

In one embodiment, in the hyaluronic acid derivative of the present disclosure, the modified histidine is Boc-histidine. Furthermore, in a specific embodiment, a graft ratio of the Boc-histidine is within 1-99% based on the total number of hydroxyl groups on the hyaluronic acid, and a graft ratio of the polymer or $C_4$-$C_{20}$ alkyl is within 1-40%.

In addition, in one embodiment, in the hyaluronic acid derivative, the preceding polymer may be polyethylene glycol (PEG), wherein a molecular weight may be about 300-10,000 Daltons. Furthermore, in this embodiment, in the hyaluronic acid derivative of the present disclosure, a graft ratio of the polymer may be within 1-40% based on the total number of hydroxyl groups on the hyaluronic acid. In a specific embodiment, the modified histidine is Boc-histidine and the preceding polymer may be polyethylene glycol (PEG), wherein a graft ratio of the Boc-histidine is within 1-80%, and a graft ratio of the polyethylene glycol (PEG) is within 1-40%.

In one embodiment, in the hyaluronic acid derivative of the present disclosure, the $C_4$-$C_{20}$ alkyl may be $C_{11}H_{23}$, and in this embodiment, a graft ratio of the $C_{11}H_{23}$ may be within 1-40% based on the total number of hydroxyl groups on the hyaluronic acid. In a specific embodiment, in the hyaluronic acid derivative of the present disclosure, the modified histidine is the Boc-histidine, and the $C_4$-$C_{20}$ alkyl may be $C_{11}H_{23}$, wherein a graft ratio of the Boc-histidine is within 1-80%, and a graft ratio of the $C_{11}H_{23}$ is within 1-40%.

In one embodiment, the polymer or $C_4$-$C_{20}$ alkyl may be bound to the hyaluronic acid through linking group(s). In another embodiment, the linking group(s) forms an ester with the hyaluronic acid. In another embodiment, the linking group(s) forms an ester with the polymer or $C_4$-$C_{20}$ alkyl. In a specific embodiment, the linking group(s) is derived from succinic anhydride, but the linking group(s) is not limited thereto.

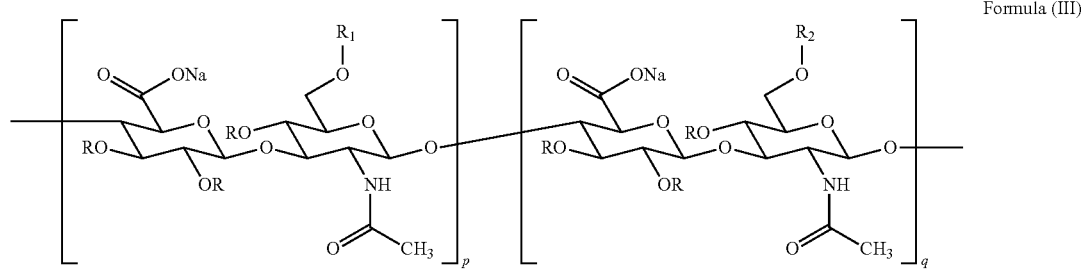

Formula (III)

A preferred embodiment of the hyaluronic acid derivative is $HA_{16k}$-g-(BocHis-co-SAmPEG$_{1.9K}$) polymer as presented in Formula (IV).

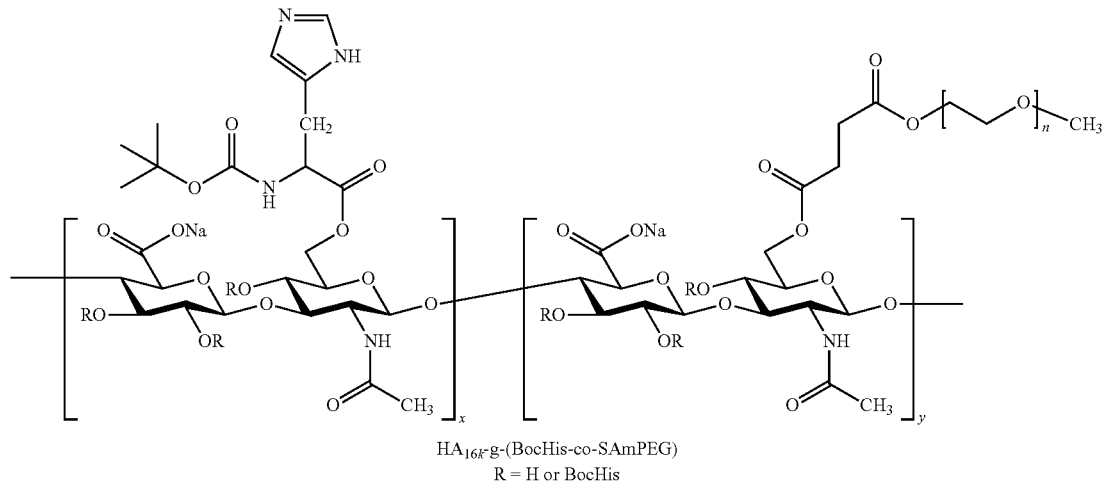

Formula (IV)

$HA_{16k}$-g-(BocHis-co-SAmPEG)
R = H or BocHis

In one embodiment of a hyaluronic acid derivative of Formula (IV), the molecular weight is about 16 kD, the grafting ratio of BocHis may be in a range within 30% to 80% based on the total number of hydroxyl groups on the hyaluronic acid, the grafting ratio of SAmPEG may be in a range within 5% to 20%, and n corresponds to n of PEG1900. A sodium carboxylate salt is one embodiment, but alternative embodiments may include other Group IA elements such as potassium.

Illustrative examples for the platinum compound may comprise, but is not limited to, one or more of dichloro(1,2-diaminocyclohexane) platinum (DACHPt), cisplatin, oxaliplatin, carboplatin, nedaplatin, phenanthriplatin and picoplatin.

Without being bound by theory, the structure of the hyaluronan nanoparticle is proposed. It is possible that the platinum compound and a carboxylate group of the hyaluronic acid derivative associate with each other due to different charges, and furthermore, by an effect at least in part from the imidazole of the modified histidine grafted on the hyaluronic acid and used to modify the hyaluronic acid, the platinum compound can be agglomerated, and make the platinum compound be packaged in the preceding hyaluronic acid derivative to form the hyaluronan nanoparticle.

In one embodiment, in the hyaluronan nanoparticle of the present disclosure, a weight ratio of the hyaluronic acid derivative to the platinum compound is about 1.25:1-50:1. In one embodiment, a weight ratio of the hyaluronic acid derivative to the platinum compound is about 1.25:1-25:1. In another embodiment, a weight ratio of the hyaluronic acid derivative to the platinum compound is about 2:1-25:1. In another embodiment, a weight ratio of the hyaluronic acid derivative to the platinum compound is about 2:1-10:1.

In one embodiment, in the hyaluronan nanoparticle, the modified histidine may be Boc-histidine and a graft ratio of the polymer or $C_4$-$C_{20}$ alkyl is 0 based on the total number of hydroxyl groups on the hyaluronic acid, (that is, the hyaluronic acid derivative only has Boc-histidine grafted thereto), and the platinum compound may be dichloro(1,2-diaminocyclohexane) platinum (DACHPt). In this embodiment, the at least one primary hydroxyl group of the hyaluronic acid which has the modified histidine grafted thereto may comprise a hydroxyl group located on the fifth carbon atom of a N-acetyl-D-glucosamine of at least one disaccharide unit of the hyaluronic acid, but is not limited thereto. Furthermore, in this embodiment, a graft ratio of the Boc-histidine may be within 1-80%, and a weight ratio of the hyaluronic acid derivative to the platinum compound is about 1.25:1-25:1.

In another embodiment, in the biomedical composition of the present disclosure, the modified histidine may be Boc-histidine, and the polymer may be polyethylene glycol (PEG), and the platinum compound may be dichloro(1,2-diaminocyclohexane) platinum (DACHPt). In this embodiment, the at least one primary hydroxyl group of the hyaluronic acid which has the modified histidine grafted thereto may comprise a hydroxyl group located on the fifth carbon atom of a N-acetyl-D-glucosamine of at least one disaccharide unit of the hyaluronic acid, but is not limited thereto. Furthermore, in this embodiment, a graft ratio of the Boc-histidine may be within 1-80%, a graft ratio of the polyethylene glycol (PEG) may be within 1-40%, and a weight ratio of the hyaluronic acid derivative to the platinum compound is about 3:1:1-50:1.

In another embodiment, in the biomedical composition of the present disclosure, the modified histidine may be Boc-histidine, and the $C_4$-$C_{20}$ alkyl may be $C_{11}H_{23}$, and the platinum compound may be dichloro(1,2-diaminocyclohexane) platinum (DACHPt). In this embodiment, the at least one primary hydroxyl group of the hyaluronic acid which has the modified histidine grafted thereto may comprise a hydroxyl group located on the fifth carbon atom of a N-acetyl-D-glucosamine of at least one disaccharide unit of the hyaluronic acid, but is not limited thereto. Furthermore, in this embodiment, a graft ratio of the Boc-histidine may be about 1-80%, a graft ratio of the $C_{11}H_{23}$ may be within 1-40%, and a weight ratio of the hyaluronic acid derivative to the platinum compound is about 2.5:1-4:1.

In one embodiment, the average particle size of the hyaluronan nanoparticle may be about 100-1000 nm. In another embodiment, the average particle size of the may be about 100-800 nm. In another embodiment, the average particle size may be about 100-500 nm. In further another embodiment, the average particle size may be about 100-300 nm. In an even further embodiment, the average particle size may be about 100, 110, 120, 130, 140, 150, 160, 170, 180, 190, 200, 210, 220, 230, 240, 250, 260, 270, 280, 290, or 300 nm.

The encapsulation efficiency of active ingredient in the hyaluronic acid derivative may be at least 50%, at least 55%, at least 60%, at least 70%, at least 75%, at least 80%, at least 85%, at least 90% or at least 95%. Encapsulation efficiency (EE %) is calculated using below formula:

Encapsulation efficiency $(EE\%) = (W_P/W_T) \times 100\%$ $W_P$ is the total amount of Pt after purification by 0.22 μm filtration (drug added–free "unentrapped drug")) and $W_T$ is the total quantity of Pt determined before purification (drug added).

The hyaluronan nanoparticle can be formulated with pharmaceutically acceptable ingredients such as carriers and excipients. Examples of pharmaceutical excipients include one or more of diluents, disintegrants, binders, lubricants and glidants.

The hyaluronan nanoparticle may be administered orally, parenterally by an inhalation spray, or via an implanted reservoir to a subject. The subject may be human or any animal with a lymphatic system, such as a mammal. The parenteral method may comprise subcutaneous, intracutaneous, intravenous, intramuscular, intra-articular, intra-arterial, intrasynovial, intrasternal, intrathecal, and intralesional, as well as infusion techniques. For different administration manners, the hyaluronan nanoparticle can be formulated into a dosage form by a conventional method.

An oral composition can comprise, but is not limited to, tablets, capsules, emulsions, and aqueous suspensions, dispersions and solutions.

In one embodiment, the administration method is an intravenous or a subcutaneous injection, preferably a subcutaneous injection. In a subcutaneous injection, it is preferred that the PDII is no greater than 2.5 (Table 2). Even more preferably, the PDII in a subcutaneous injection is no greater than 0.5.

In one embodiment, the administration dose may be within 0.01 to 10 mg Pt/kg, preferable dosages ranges are within 0.05 to 5 mg Pt/kg, and more preferable within 0.1 to 5 mg/kg, and even more preferable within 0.1 to 3 mg/kg. Specific dosages may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 mg Pt/kg.

In one embodiment, the tumor is metastatic. In another embodiment the metastatic tumor may be melanoma, head and neck cancer, breast cancer, prostate cancer, lymphoma, gastric cancer, colorectal cancer, ovarian cancer, uterine cancer, or lung cancer, but is not limited thereto.

In another embodiment, the volume of the tumor treated by the hyaluronan nanoparticles is 30% or less, 25% or less, 20% or less, 15% or less, 10% or less, or 5% or less of the untreated volume of the tumor. In yet another embodiment, the volume of the tumor treated by the hyaluronan nanoparticles is 30% or less, 25% or less, 20% or less, 15% or less, 10% or less, or 5% or less of the original volume of the tumor.

EXAMPLES

Materials
Sources of Materials
Sodium hyaluronate (MW: 16 kD) and $HA_{16k}$-g-(BocHis-co-SAmPEG$_{1.9K}$) polymer were provided by Material and Chemical Research Laboratories, ITRI. Dichloro(1,2-diamminocyclohexane) platinum(II) (DACHPt), $AgNO_3$, and the platinum (Pt) standard were purchased from Sigma-Aldrich (St. Louis, Mo.). Cisplatin (CDDP) was purchased from Spectrum Chemical Manufacturing Corp. Oxalip injection (oxaliplatin) was purchased from TTY Biopharm. Murine melanoma cell line, B16-F10-luc2, was purchased from Caliper LifeSciences (Hopkinton, Mass.). Human head and neck cancer cell line, SAS-LN, was a gift from Dr. Muh-Hwa Yang's lab in National Yang-Ming University. RPMI1640, DMEM media, and fetal bovine serum were from GIBCO BRL (Grand Island, N.Y.). C57BL/6 (C57BL/6NCrlBltw) and BALB/c nude (CAnN.Cg-Foxn1nu/Crl-Bltw) mice were purchased from BioLASCO Ltd (Ilan, Taiwan). CD44 antibody (Cat. MA4400) was purchased from Thermo Scientific.
Methods
Preparation of PtHC604
Dichloro(1,2-diaminocyclohexane)platinum(II) (DACHPt) was suspended in distilled water and mixed with silver nitrate ($[AgNO_3]/[DACHPt]$=2) in the dark at 25° C. for 24 hours to form the aqueous complex. Silver chloride (AgCl) precipitates were removed by centrifugation followed by filtration through a 0.22 μm filter. PtHC604 formulation was prepared by mixing DACHPt and $HA_{16k}$-g-(BocHis-co-SAmPEG1.9K) polymer (Formula (IV)) in the distilled water with a molar ratio of 1/3 (drug to polymer). The molecular weight of HA was determined by size-exclusion chromatography (SEC) with multi-angle laser light scattering (MALS). $HA_{16k}$ had an average molecular weight of 16 kD. The "graft ratio" is the average percentage of substituent grafting on the total number of hydroxyl group over total repeat unit of HA. The grafting ratio of BocHis was located in the range from 40% to 60%. In addition, the grafting ratio of SAmPEG was located in the range from 6% to 13%.
Preparation of PtHC16001
Dichloro(1,2-diaminocyclohexane)platinum(II) (DACHPt) was suspended in distilled water and mixed with silver nitrate ($[AgNO_3]/[DACHPt]$=2) in the dark at 25° C. for 24 hours to form the aqueous complex. Silver chloride (AgCl) precipitates were removed by centrifugation followed by filtration through a 0.22 μm filter. PtHC16001 formulation was a control group which was prepared by mixing DACHPt and native $HA_{16k}$ polymer in the distilled water with a molar ratio of 1/3 (drug to polymer).
Preparation of CPHC008
CPHC008 formulation was prepared by mixing cisplatin (CDDP) powders and $HA_{16k}$-g-(BocHis-co-SAmPEG$_{1.9K}$) polymer in distilled water with a molar ratio of 1/3.5 (drug to polymer). The grafting ratio of BocHis was located in the range from 40% to 60%. In addition, the grafting ratio of SAmPEG was located in the range from 6% to 13%. The preparation process was conducted in the dark at 25° C. with a continuous stirring for 72 hours. The mixture was sonicated and purified by ultrafiltration and 0.22 μm filtration.
Particle Size Measurement
The particle sizes of HA-based nanoparticles were determined using dynamic light scattering (DLS) measurement (ZetaPlus, BROOKHAVEN).

Encapsulation Efficiency

The amounts of Pt were quantified by ICP-OES in preparation process. Encapsulation efficiency (EE %) was calculated using below formula:

Encapsulation efficiency $(EE\%) = (W_P/W_T) \times 100\%$ $W_P$ is the total amount of Pt after purification by 0.22 µm filtration (drug added–free "unentrapped drug")) and $W_T$ is the total quantity of Pt determined before purification (drug added).

In Vitro Release Assay

The release of platinum drug from HA-based nanoparticles in physiological saline (PBS, pH 7.4, 150 mM NaCl) at 37° C. was evaluated by the dialysis method (molecular weight cutoff size: 3500, Spectrum Laboratories, Inc.). The Pt content in dialysate was sampled at defined time periods and measured by ICP-OES (Thermo Icap 6000 SERIES).

In Vitro Cytotoxicity Assay

B16-F10-luc2 cells were cultured in RPMI1640 medium supplemented with 10% heat-inactivated fetal bovine serum and maintained in a humidified 37° C., 5% $CO_2$ incubator. B16-F10-luc2 cells were seeded on 96-well plate for $2 \times 10^3$ cells per well and incubated overnight at 37° C. Cells were treated with phosphate-buffered saline (PBS), oxaliplatin, or PtHC604 for 48 hours at 37° C. Cell viability was determined by MTT assay.

CD44 Receptor Expression

The flow cytometric method was used for determining CD44 receptor expression on different cells (RPMI2650, SCC9 and GBM8401). The cells were treated with an anti-CD44 antibody and stained with a fluorescence-conjugated secondary antibody. The mean fluorescence intensities were analyzed separately by gating on subset-specific regions.

CD44 Targeting Characterization

To verify the CD44 targeting ability of PtHC604, three distinct CD44 expression cells (RPMI2650, SCC9 and GBM8401) were used for the cellular binding/uptake study. $2 \times 10^5$/mL cells were seeded on 12 well plates and incubated overnight at 37° C. PtHC604 (50 µM Pt) were applied to three different cells and incubated in serum-free medium at 37° C. for 2 h. For the competition experiments, GBM8401 cells were pretreated with CD44 antibody (5 µg/mL) or HA (12 mg/mL) for 1 h before the addition of PtHC604. After PtHC604 incubation for 2 h, the cells were washed three times with medium and harvested for cellular platinum analysis by ICP-MS.

Lymphatic Delivery of PtHC604 By Different Injection Routes

To investigate the lymphatic delivery in different injection routes, Sprague Dawley (SD) rats were injected intravenously with PtHC604 or oxaliplatin in a dose of 4 or 9 mg Pt/kg, respectively. Anesthetic SD rats by isoflurane were injected subcutaneously into the right mammary fat pad with PtHC604 (1 mg Pt/kg). After 4, 24, 48, 72 and 96 hours post-injection, animals were euthanized by $CO_2$. Right axillary lymph nodes were harvested and stored at −80° C. until analysis. Platinum concentration in lymph nodes was analyzed by ICP-MS (THERMO XSERIES II).

Lymphatic Delivery of PtHC604 by Subcutaneous Injection in Normal Rats

To evaluate the lymphatic delivery, SD rats were placed under isoflurane anesthesia and injected subcutaneously into the right mammary fat pad with PtHC604, PtHC16001 or oxaliplatin (1 mg Pt/kg). After 4, 24, 48, 72 and 96 hours post-injection, animals were euthanized by $CO_2$. Right axillary lymph nodes, sciatic nerves and plasma were harvested and stored at −80° C. until analysis. Platinum concentrations in lymph nodes and sciatic nerves were analyzed by ICP-MS. Platinum concentration in plasma was analyzed by ICP-OES.

Residual Drug in Injection Site Evaluation

To evaluate residual drug in the injection site, BALB/c mice were subcutaneously injected into the left hind of footpad with PtHC604 or oxaliplatin (1 mg Pt/kg). After 4, 24, 48, and 96 hours post-injection, animals were euthanized by $CO_2$. Each foot was harvested and stored at −80° C. until analysis. Platinum concentration in each foot was analyzed by ICP-MS.

In Vivo Survival Rate and Anti-Lymphatic Metastasis in Spontaneous Lymphatic Metastasis Model of B16-F10-luc2

Prior inoculation of the cells, B16-F10-luc2 cells were harvested during the exponential growth period and washed twice with sterile PBS, and then suspended in PBS with 50% Matrigel (BD Biosciences). Respective $3 \times 10^5$ B16-F10-luc2 cells were implanted subcutaneously into the right hind foot pad of female C57BL/6 mice (6 to 8 weeks old). B16-F10-luc2 tumors were allowed to grow for 5 weeks, and the tumor cells spontaneously metastasized to regional popliteal lymph node. Lymphatic metastasis was confirmed by bioluminescence imagine using IVIS spectrum. Oxaliplatin was administered by intravenous or subcutaneous injection at the dose of 3 mg Pt/kg, and PtHC604 was administered by subcutaneous injection into the footpad at the same dose of 3 mg Pt/kg. All test articles were administrated twice a week for 2 weeks (n=6-8/group in one independent experiment). Tumor size was measured by calipers and converted into tumor volume using the following formula: $V=LS^2/2$ (where L is the longest diameter and S is the shortest diameter). Death was defined when mice dead or tumor volumes were >3000 mm³. At the end of study, mice were sacrificed and the popliteal lymph node was collected for measurement. The volume of lymph node was measured by the same formula above: $V=LS^2/2$.

In Vivo Anti-Lymphatic Metastasis in Spontaneous Lymphatic Metastasis Model of SAS-LN SAS-LN cells transfected with luciferase were suspended in PBS and were orthotropic implanted ($2 \times 10^5$ cells per mouse) into the tongue of female BALB/c nude mice (6 to 8 weeks old). SAS-LN tumors were allowed to grow for 1 week. Cisplatin was administered by intravenous injection at dose of 3 mg Pt/kg, and CPHC008 was administered by subcutaneous injection into the buccal site at dose of 3 mg Pt/kg (n=10/group). All test articles were administrated once a week for 5 weeks. After sacrifice, cervical lymph nodes were collected to evaluate metastasis by bioluminescence imagine using IVIS.

Local Toxicity Assessment of PtHC604

To evaluate the local toxicities, Female BALB/c mice were subcutaneously injected into the left hind foot pad by PtHC604 and oxaliplatin. Mice were weighted and grouped into (1) vehicle; (2) 0.3 mg Pt/kg oxaliplatin; (3) 1 mg Pt/kg oxaliplatin; (4) 3 mg Pt/kg Oxaliplatin; (5) 0.3 mg Pt/kg PtHC604; (6) 1 mg Pt/kg PtHC604; (7) 3 mg Pt/kg PtHC604, n=6/group. Each animal was treated once weekly for 4 weeks. The skin toxicities in the injection site were measured by erythema and oedema grading (Table 1). The skin toxicities potential was evaluated using Primary Dermal Irritation Index (PDII) by combining erythema and oedema grading, and classified into non-irritant, negligible-irritant, mild irritant, moderate irritant, and severe irritant (Table 2).

TABLE 1

Grading of skin reactions - Acute dermal irritation

| Erythema and eschar formation | Oedema formation |
|---|---|
| 0-No erythema | 0-No oedema |
| 1-Very slight erythema (barely perceptible) | 1-Very slight oedema (barely perceptible) |
| 2-Well defined erythema | 2-Slight oedema (edges of area well-defined by definite raising) |
| 3-Moderate to severe erythema | 3-Moderate oedema (raised approximately 1 mm) |
| 4-Severe erythema (beet redness) to eschar formation (injuries in depth) | Severe oedema (raised more than 1 mm and extending beyond area of exposure) |

TABLE 2

Classification of dermal irritation potential

| PDII | Classification |
|---|---|
| 0.0 | Non-irritant |
| >0.0-0.5 | Negligible irritant |
| >0.5-2.5 | Mild irritant |
| >2.5-5.0 | Moderate irritant |
| >5.0-8.0 | Severe irritant |

Results

The Composition of Different Formulations

In this system, without being bound by theory, the driving force for the metal-polymer ionic complex formation may be not only by ionic force but also the Boc-His. DACHPt or cisplatin was encapsulated into HA-based nanoparticles with an efficiency of 70±10%. The PtHC16001 incorporated the native HA polymer to form the formulation as control. The compositions of different HA-based nanoparticles are summarized in Table 1.

TABLE 3

The compositions of different HA-based nanoparticles

| Formulation code | Polymer | Drug | [Polymer COOH]:[Pt] | Particle size (nm) | Encapsulation efficiency (%) |
|---|---|---|---|---|---|
| PtHC16001 | HA$_{16k}$ | DACHPt | 3:1 | 200 ± 50 | — |
| PtHC604 | HA$_{16k}$-g-(BocHis-co-SAmPEG$_{1.9K}$) | DACHPt | 3:1 | 150 ± 50 | 70 ± 10 |
| CPHC008 | HA$_{16k}$-g-(BocHis-co-SAmPEG$_{1.9K}$) | Cisplatin | 3:1 | 200 ± 50 | 70 ± 10 |

In Vitro Release Study

The release behavior of platinum drug from HA-based nanoparticles was studied by dialysis in PBS (FIG. 1). The platinum release from HA-based nanoparticles is inversely proportional to the BocHis ratio, indicating the BocHis on HA has an important role in the particle stabilization. About 30-40% platinum was released from PtHC604 after incubation in PBS for 24 hours, whereas about 85% platinum was released from PtHC16001.

Cytotoxicity of Oxaliplatin and PtHC604 in B16-F10-luc2 Cells In Vitro

Figure 2:
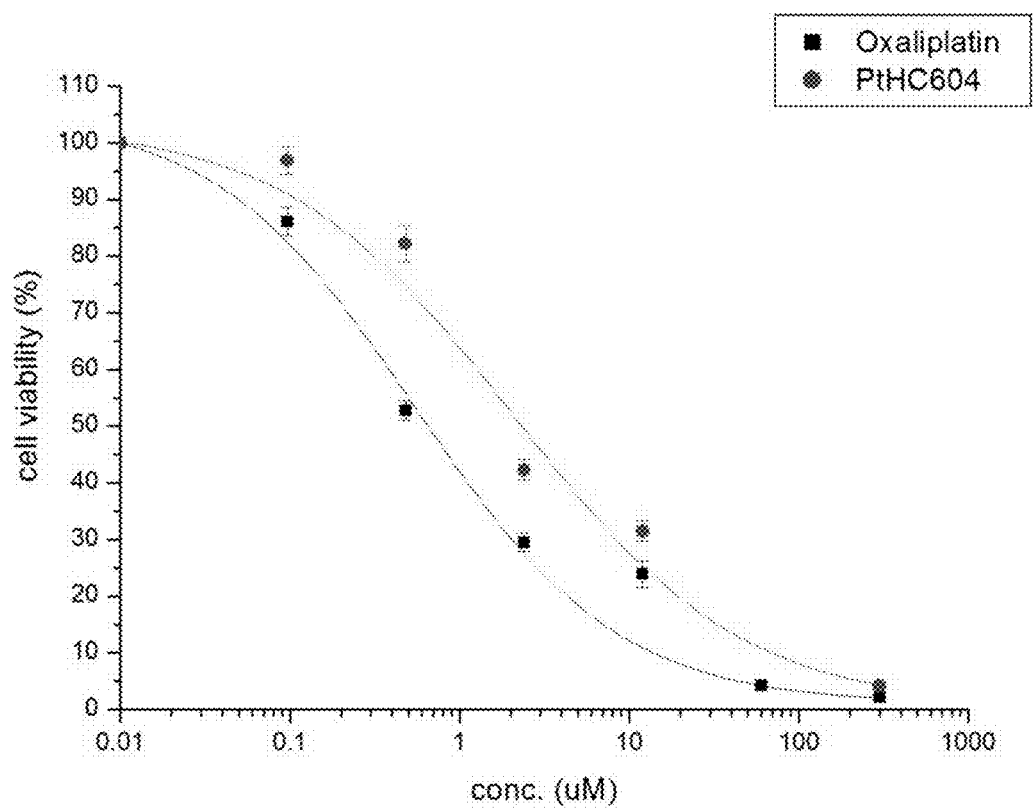
FIG. 2. shows in vitro cytotoxicity of oxaliplatin and PtHC604 in B16-F10-luc2 cells.

The cytotoxicity of PtHC604 was evaluated in comparison to oxaliplatin in B16-F10-luc2 cells for 48 hours. The IC$_{50}$ values, calculated from concentration-survival curves obtained after 48 h treatment from the MTT assay, were investigated. PtHC604 showed a growth inhibitory potency that was lower than that of oxaliplatin (Table 4 and FIG. 2).

TABLE 4

The IC$_{50}$ of oxaliplatin and PtHC604 in B16-F10-luc2 cells

| | IC$_{50}$ (µM) |
|---|---|
| Oxaliplatin | 0.65 |
| PtHC604 | 2.28 |

PtHC604 Target CD44 Positive Cells

Figure 3A:
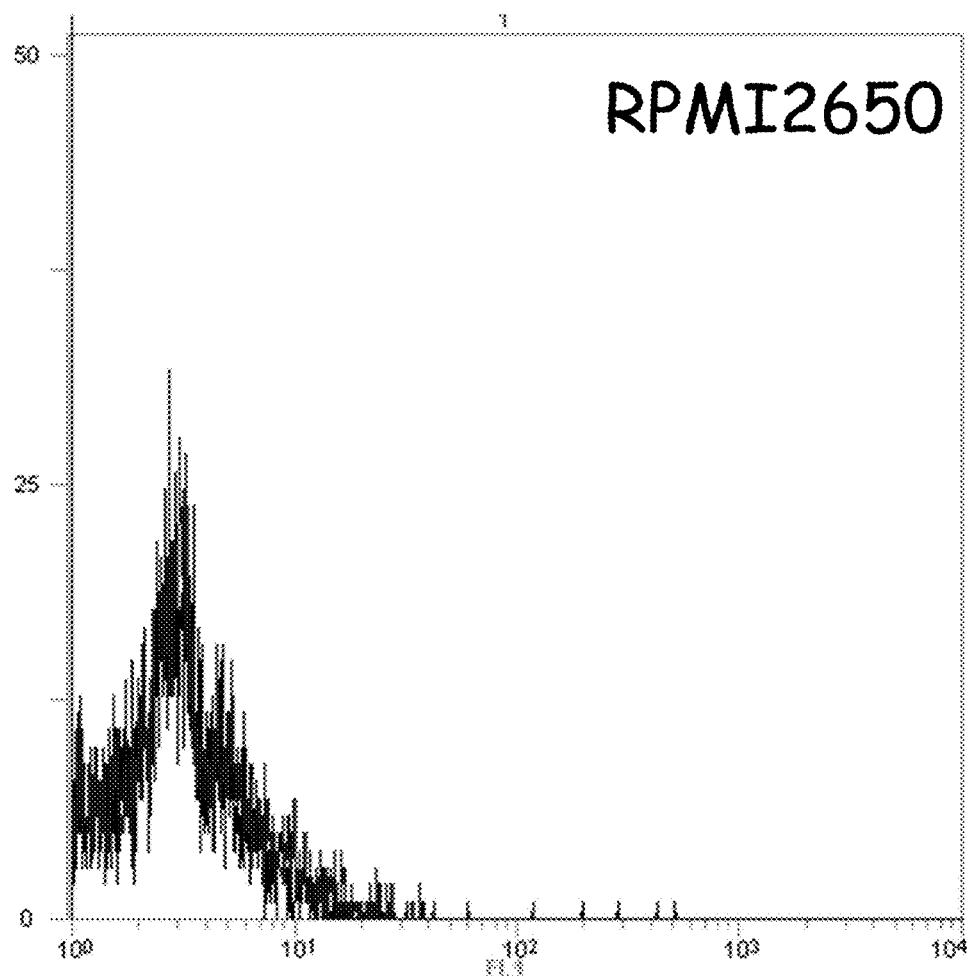
FIGS. 3A, 3B and 3C show CD44 expression in RPMI2650 (FIG. 3A), SCC9 (FIG. 3B) and GBM8401 cell lines (FIG. 3C), respectively.
Figure 3B:
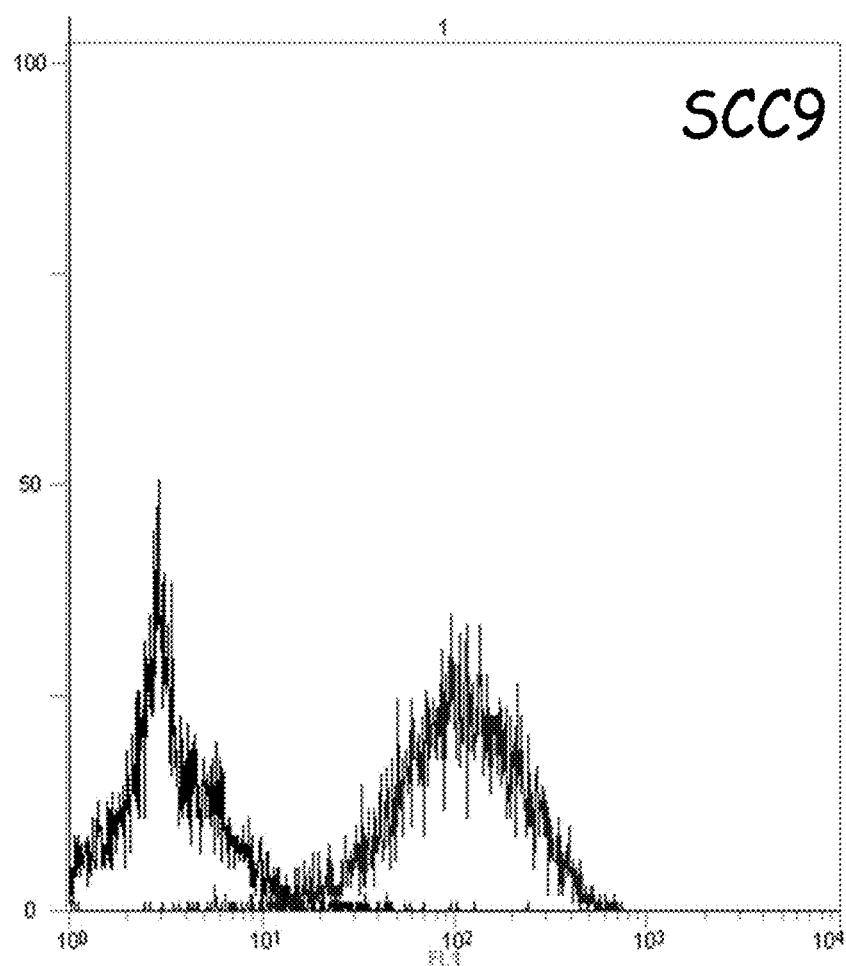
Figure 3C:
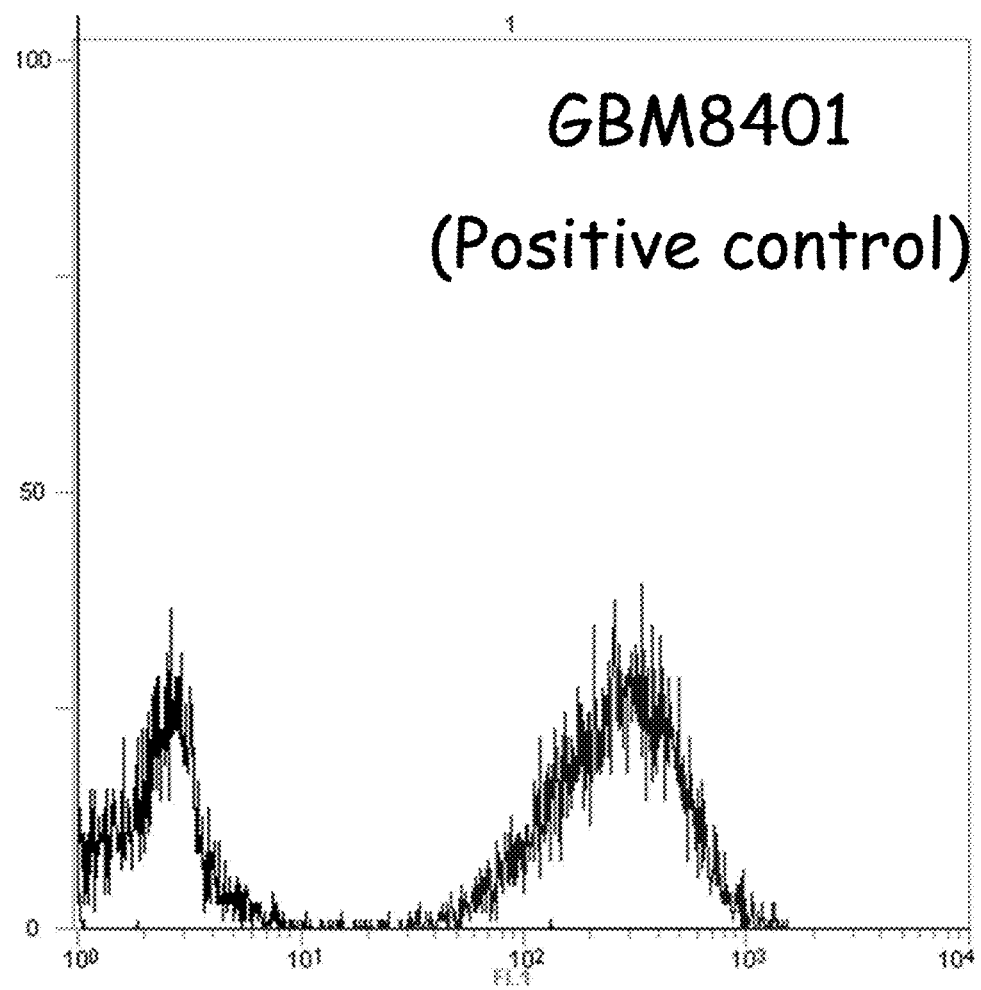
Figure 4:
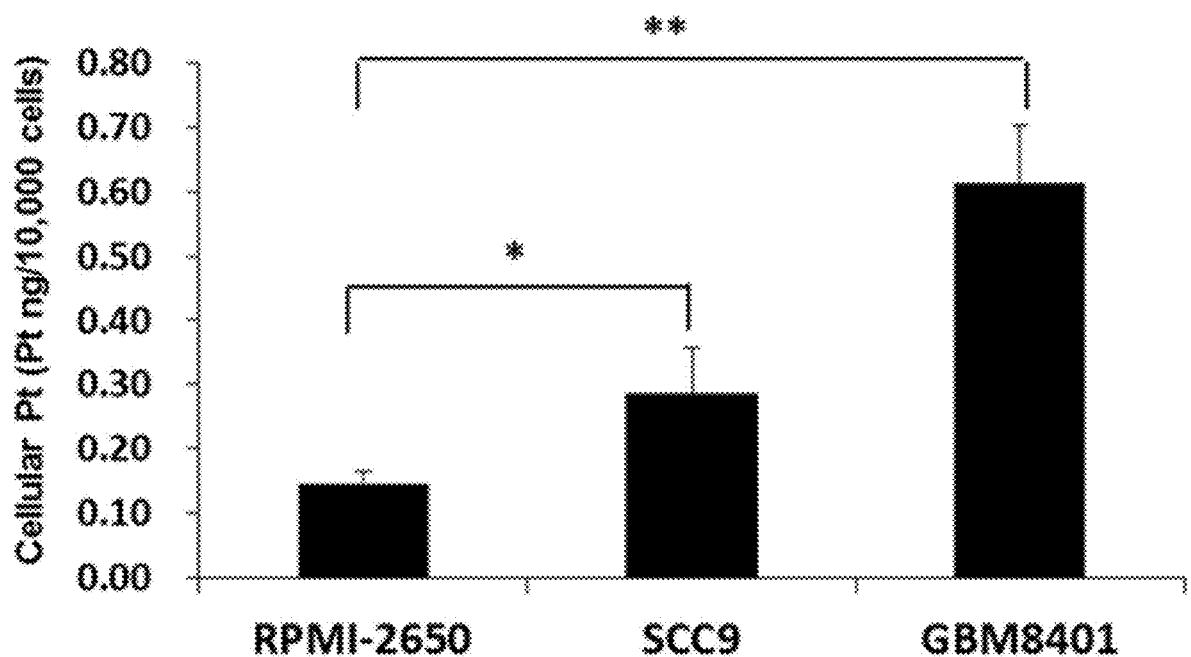
FIG. 4. shows cellular Pt determination after PtHC604 treatment in cell lines with various CD44 expression levels.
Figure 5:
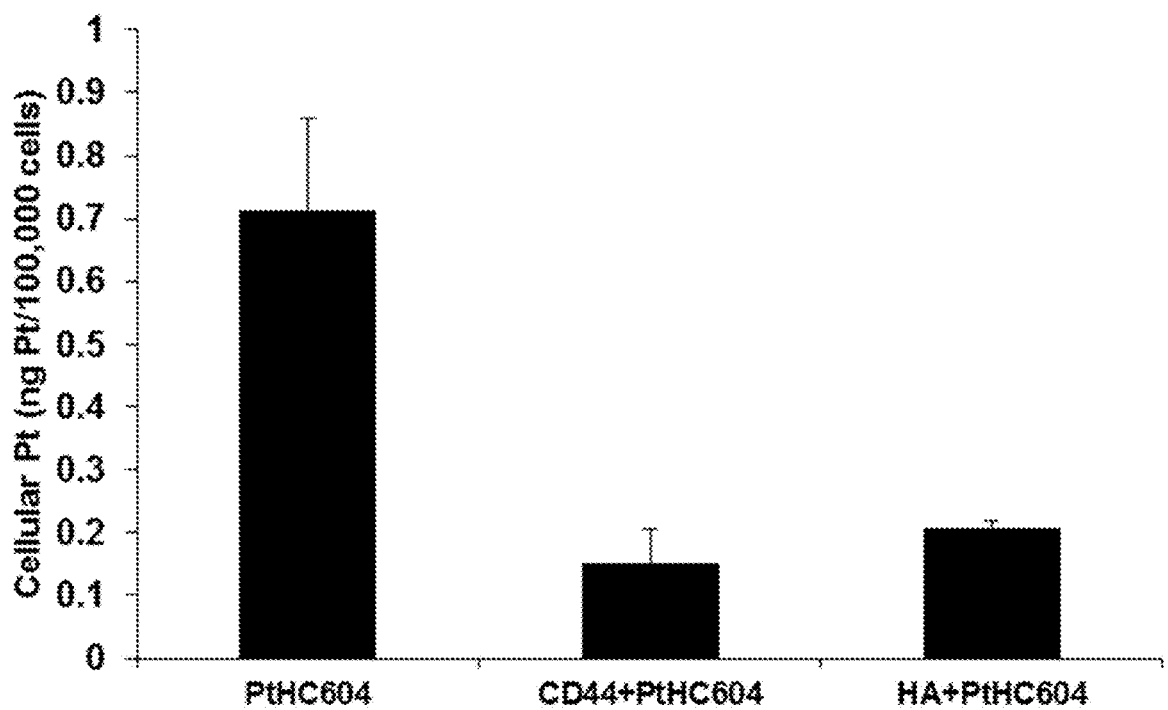
FIG. 5. shows the cellular Pt in GBM8401 using anti-CD44 Ab or HA competition.

The CD44 targeting result showed that GBM cells had the highest Pt content compared to CD44 negative (RPMI2650) and medium level expressed cells (SCC9). This indicated cellular Pt content after PtHC604 treatment positively correlated with CD44 expression (FIGS. 3 and 4). Moreover, cellular Pt in GBM8401 cell (high CD44 expression) could be detected in the PtHC604 treated group. CD44 antibody or native HA-pretreated cells demonstrated a 79% and a 72% reduction in the relative Pt concentration compared to the non-treated cells, respectively (FIG. 5). The cellular uptake test showed the targeting ability of PtHC604 for CD44 expressing cells. This competition study demonstrated PtHC604 at least maintained the ability of hyaluronic acid to interact with CD44.

Lymphatic Delivery of PtHC604 by Different Injection Routes

Figure 6:
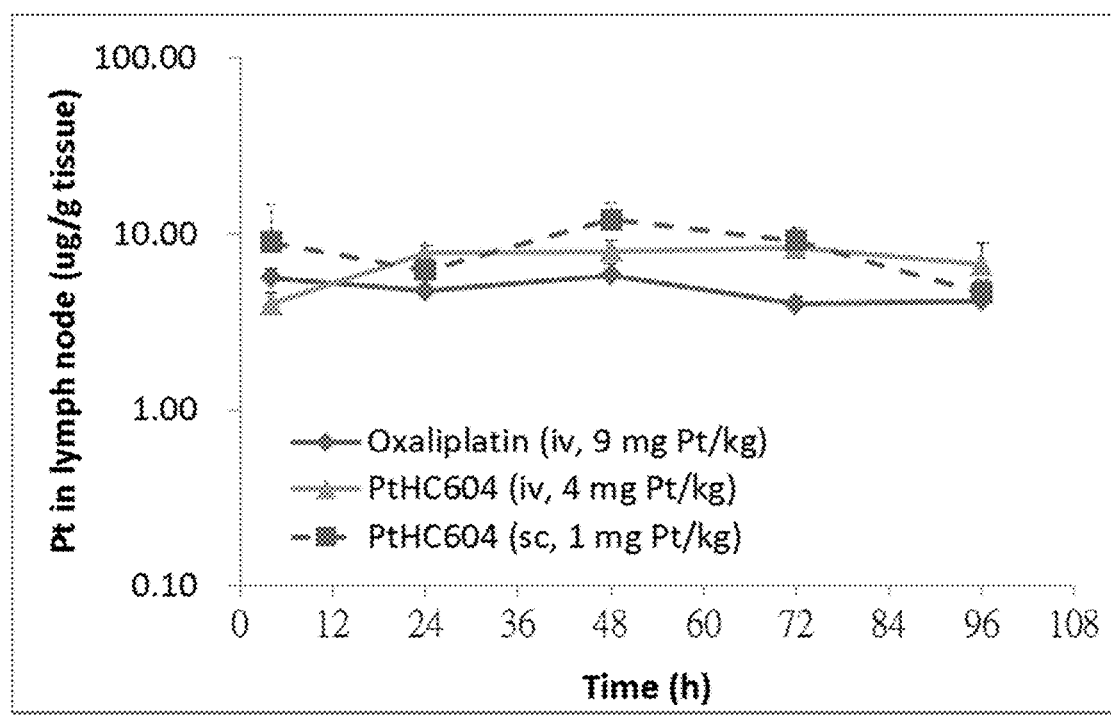
FIG. 6. shows the lymphatic Pt profiles through intravenous or subcutaneous administration.

Mice subcutaneously injected with PtHC604 had the highest area under curve (AUC) compared with intravenous injection with PtHC604 and oxaliplatin (FIG. 6). Note that oxaliplatin was administered by intravenous injection at 9 times the amount of Pt/kg and PtHC604 was administered by intravenous injection at 4 times the amount of platinum Pt/kg compared to PtHC604 by subcutaneous injection. Normalization with dose, the lymphatic exposure of PtHC604 after subcutaneous injection was 4.6 and 15.6 folds higher than that of PtHC604 by intravenous injection and oxaliplatin by intravenous administration, respectively (Table 5). The results indicated lymphatic delivery of PtHC604 improved drug level in the local lymph nodes compared to intravenous oxaliplatin dosing. PtHC604 by subcutaneous administration greatly increased lymph node basin concentrations, suggesting the carriers is able to deliver platinum to lymph nodes through the lymphatics much more effectively than intravenous dosing route.

TABLE 5

Lymphatic exposure of PtHC604 using intravenous (iv) and subcutaneous (sc) dosing

| | Oxaliplatin | PtHC604 | PtHC604 |
|---|---|---|---|
| Dosing route | iv | iv | sc |
| Dose (mg Pt/kg) | 9 | 4 | 1 |
| Lymphatic AUC$_{0-96\ h}$ (h * ug/g) | 468.7 | 698.6 | 809.7 |

TABLE 5-continued

Lymphatic exposure of PtHC604 using intravenous (iv) and subcutaneous (sc) dosing

| | Oxaliplatin | PtHC604 | PtHC604 |
|---|---|---|---|

*Animals received maximum tolerance doses through iv dosing route

Lymphatic Delivery of PtHC604 by Subcutaneous Injection

Figure 7:
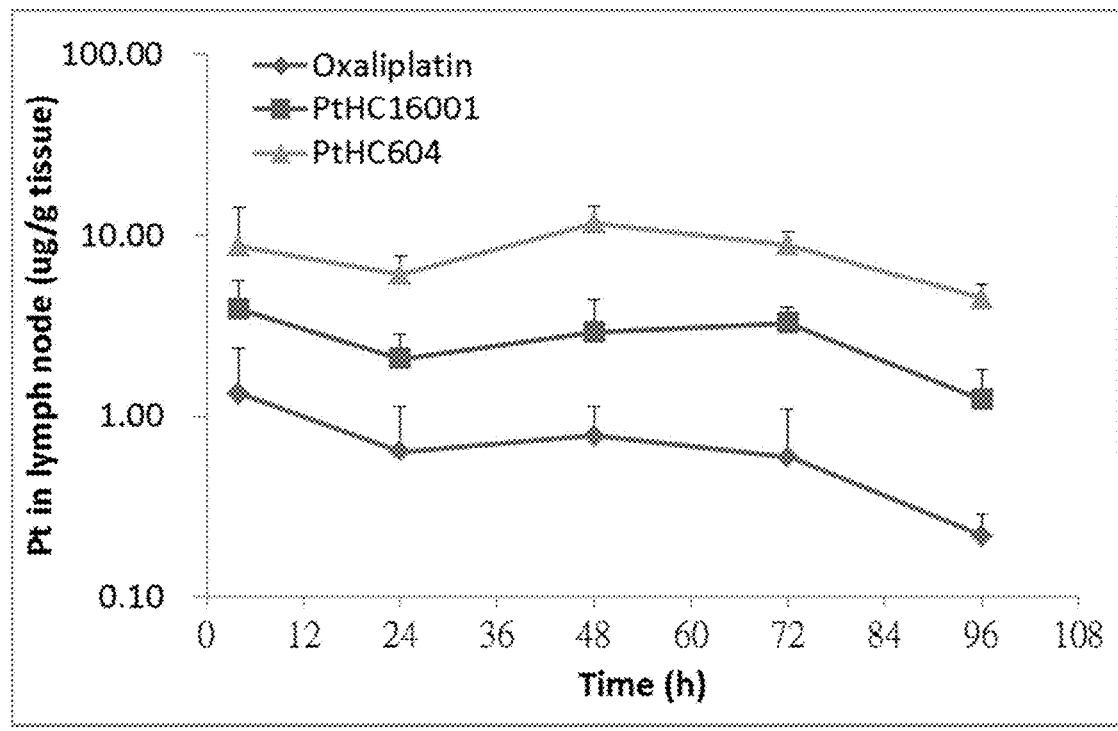
FIG. 7. shows the lymphatic Pt profiles of PtHC604, PtHC16001, and oxaliplatin through subcutaneous administration.

After mammary fat pad injection, the platinum in the axillary lymph node was higher in PtHC604 group than oxaliplatin and PtHC16001 groups (Table 6 and FIG. 7). The area under curve of platinum in the axillary lymph node after injected with PtHC604 increase 11 and 2 times compared with oxliplatin and PtHC16001, respectively. Therefore, PtHC604 showed increased accumulation in the metastatic tumor compared with oxaliplatin. PtHC604 appeared to maintain its stability in vivo long enough to traffic or localize into the lymphatics before releasing its conjugated drug. Oxaliplatin had the lowest Pt exposure in plasma compared with PtHC16001 and PtHC604. Pt encapsulated in HA-based carriers might protect Pt drug left from blood vessel. PtHC604 showed lower platinum exposure in sciatic nerve compared with oxaliplatin and PtHC16001. These results indicated PtHC604 might have less systemic toxicity concern and be more efficacious than oxaliplatin.

TABLE 6

Melanoma tissue exposure of PtHC604, PtHC16001, and oxaliplatin through subcutaneous dosing

| | AUC (96 h) (h * ug/g) | | |
|---|---|---|---|
| Tissue | PtHC16001 | Oxaliplatin | PtHC604 |
| Lymph node | 265.1 | 66.0 | 787.3 |
| Plasma | 26.0 | 6.7 | 16.0 |
| Sciatic nerve | 10.4 | 12.0 | 7.3 |

Residual Drug Evaluation

Figure 8:
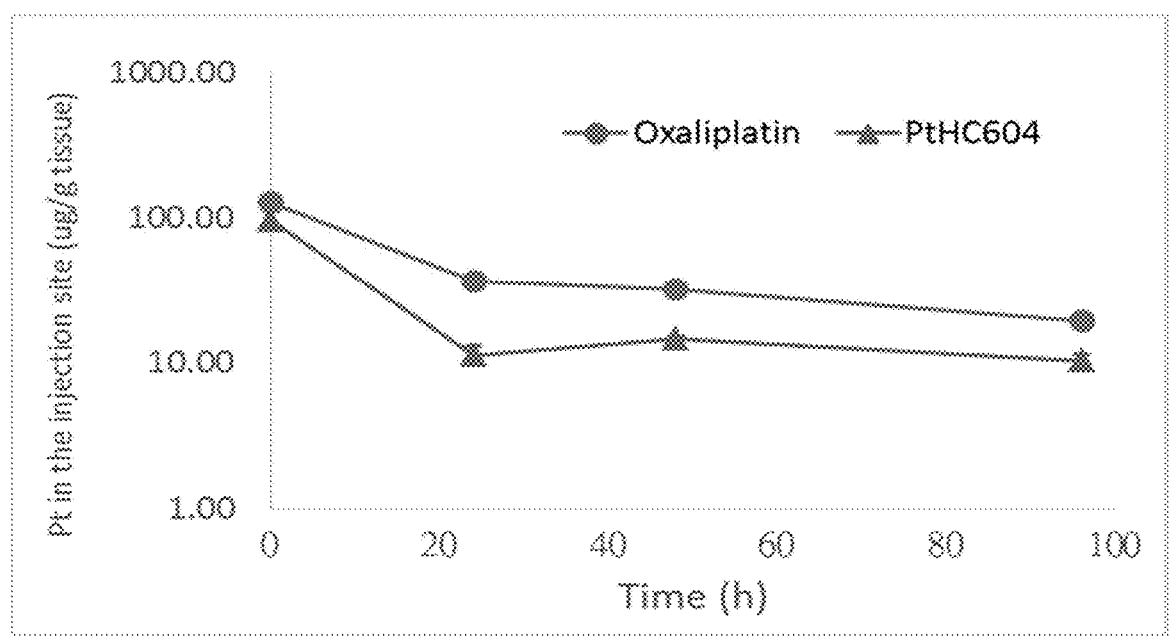
FIG. 8. shows the residual Pt in injection site after mice subcutaneously injected with oxaliplatin or PtHC604 into the right hind foot pad.

After left hind of footpad injection with PtHC604 and oxaliplatin, the Pt content of platinum in the foot decreased with time. At 24 hour after injection with PtHC604 and oxaliplatin, 12% and 29% residual Pt was detected in the foot, respectively (FIG. 8). The Pt exposure in the foot were 2212 and 4089 h*ug/mL after PtHC604 and oxaliplatin injection, respectively. The lower residual Pt of PtHC604 might hint lower local toxicities.

Figure 9:
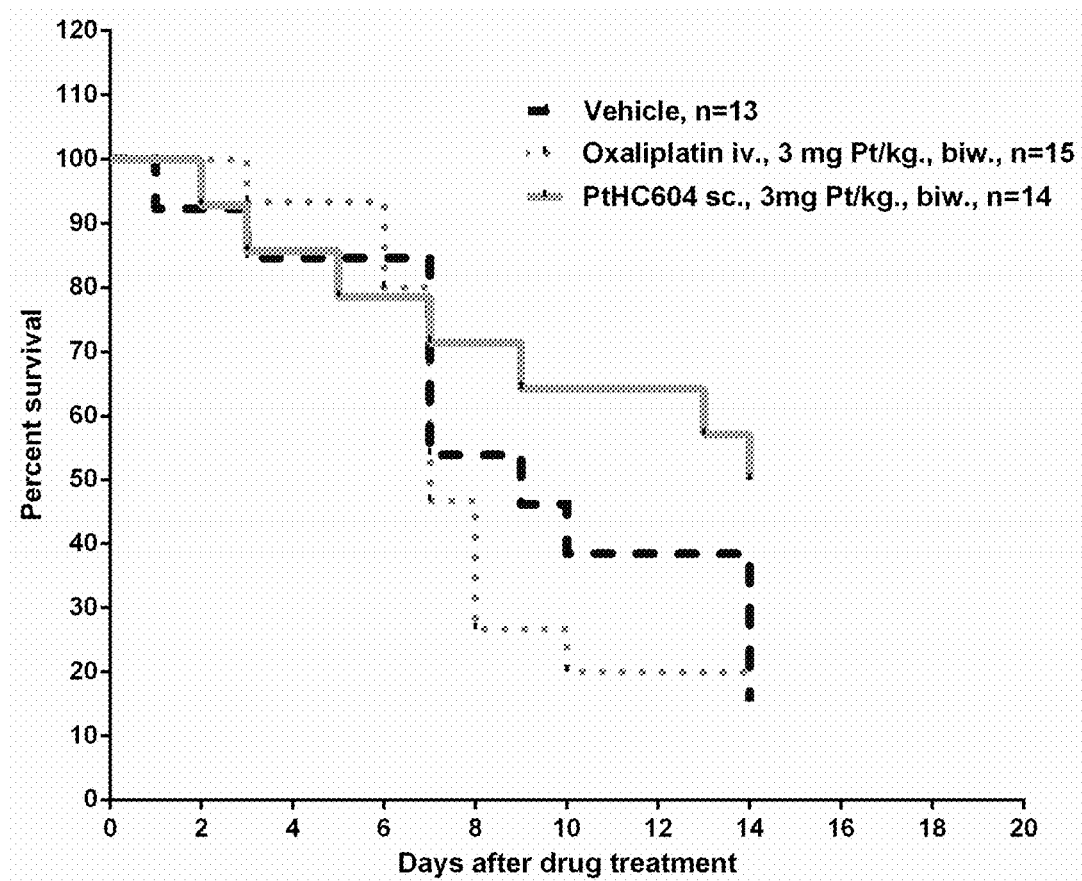
FIG. 9. shows the survival rate of mice subcutaneously administrated with oxaliplatin or PtHC604.
Figure 10:
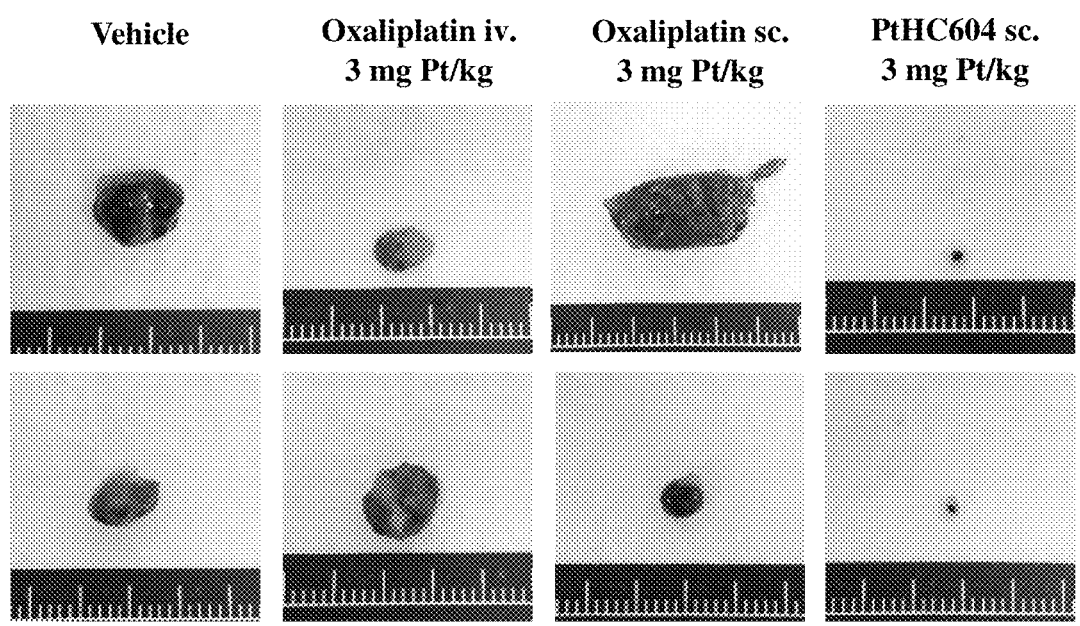
FIG. 10. shows the representative popliteal nodes after melanoma bearing mice subcutaneously injected with PtHC604, intravenously treated with oxaliplatin or subcutaneously injected with oxaliplatin.
Figure 12:
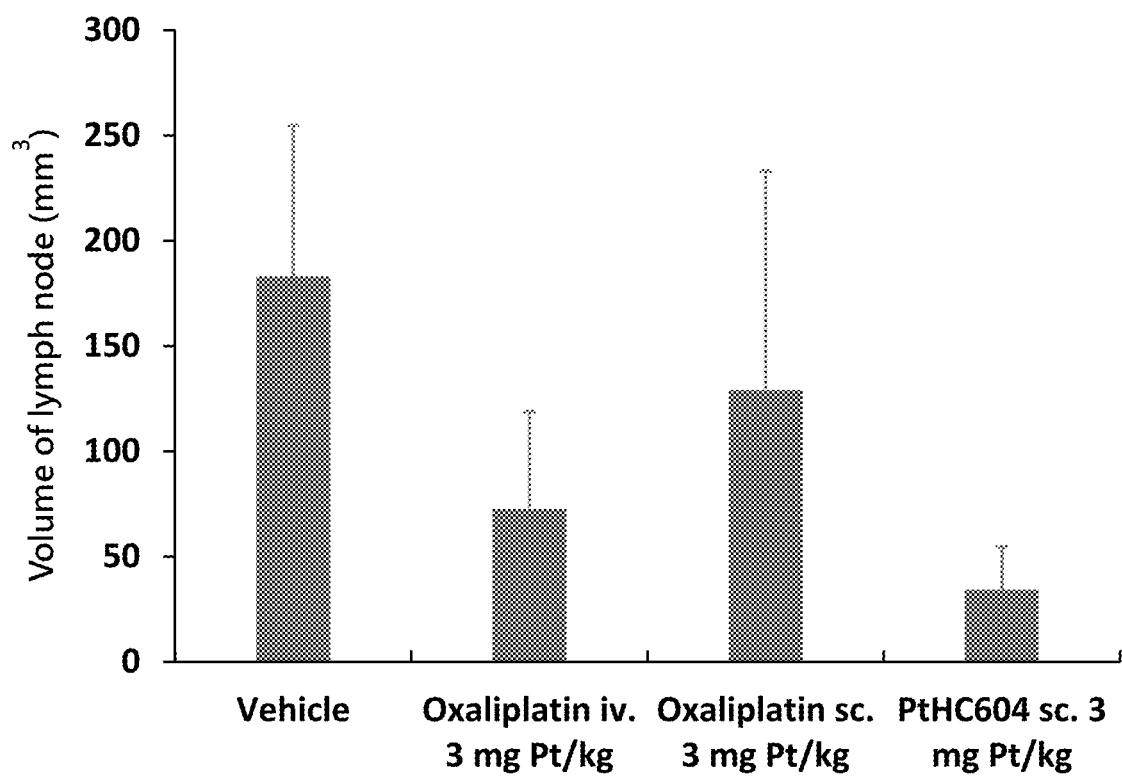
FIG. 12. shows the volume of lymph node after oxaliplatin and PtHC604 treatment by intravenous and subcutaneous injection, respectively.

Survival Rate and Anti-Lymphatic Metastasis of PtHC604 in Spontaneous Lymphatic Metastasis Model of B16-F10-luc2 In Vivo:

Murine melanoma cell line, B16-F10-luc2, was inoculated in the hind foot pad of immunocompetent syngeneic C57BL/6 mice, and spontaneously metastasizing to regional popliteal lymph node. Oxaliplatin was intravenously or subcutaneously injected, and PtHC604 was local subcutaneously injected in the footpad for local lymphatic delivery. The survival rate and median survival days after treatment were shown in FIG. 9 and Table 7. The median survival days after treatment of vehicle, intravenous injection of oxaliplatin, and subcutaneous injection of PtHC604 were 9, 7, and 14 days, respectively. Subcutaneously administration PtHC604 can prolong survival of mice. After administration for 2 weeks, mice were sacrificed and the popliteal lymph node was collected (FIG. 10). PtHC604 by subcutaneous injection could reduce the volume of metastatic lymph node compared with oxalipaltin by intravenous and subcutaneous administration. The volume of popliteal lymph node treated with vehicle, intravenous injection of oxaliplatin, subcutaneous injection of oxaliplatin, and subcutaneous injection of PtHC604 were 183.2±71.7, 72.7±46.2, 129.2±103.9, 34.3±20.3 mm$^3$ (mean±SEM), respectively (FIG. 12). Based on the superiority of lymphatic delivery, PtHC604 demonstrated obvious efficacy of anti-lymphatic metastasis in vivo, although PtHC604 showed a lower growth inhibitory potency than oxaliplatin in vitro.

TABLE 7

The median survival days of mice bearing metastatic melanoma administrated with oxaliplatin or PtHC604

| | Median survival days |
|---|---|
| Vehicle, n = 13 | 9 |
| Oxaliplatin iv., 3 mg Pt/kg, biw, n = 15 | 7 |
| PtHC604 sc., 3 mg Pt/kg, biw., n = 14 | 14 |

Anti-Lymphatic Metastasis of CPHC008 in Spontaneous Lymphatic Metastasis Model of SAS-LN In Vivo:

Cisplatin is the standard therapy for head and neck cancer. For evaluation of anti-metastasis in head and neck cancer, CPHC008 and cisplatin were used. After SAS-LN inoculated in tongue for 7 days, BALB/c nude mice were injected with CPHC008 subcutaneously or cisplatin intravenously once weekly for 5 weeks. At the end of study, the cervical lymph nodes were harvested and metastasis determined by IVIS ex vivo. The metastatic ratio of vehicle, cisplatin, and CPHC008 was 90%, 78%, 10%, respectively (Table 8). CPHC008 through subcutaneous injection showed the better lymphatic metastatic inhibition compared with cisplatin. That indicated CHPC008 might deliver higher platinum level in lymph nodes to result in better metastasis inhibition than cisplatin. These results indicated CPHC008 could be the potential candidate better than standard therapy of head and neck cancer in treating lymphatic metastasis.

TABLE 8

Anti-lymphatic metastasis of CPHC008 and cisplatin in metastatic mice bearing SAS-LN

| | Lymphatic metastasis |
|---|---|
| Vehicle, n = 10 | 90% |
| Cisplatin iv., 3 mg Pt/kg, qw., n = 9 | 78% |
| CPHC008 sc., 3 mg Pt/kg, qw., n = 10 | 10% |

Local Toxicity Assessment of PtHC604

Figure 11:
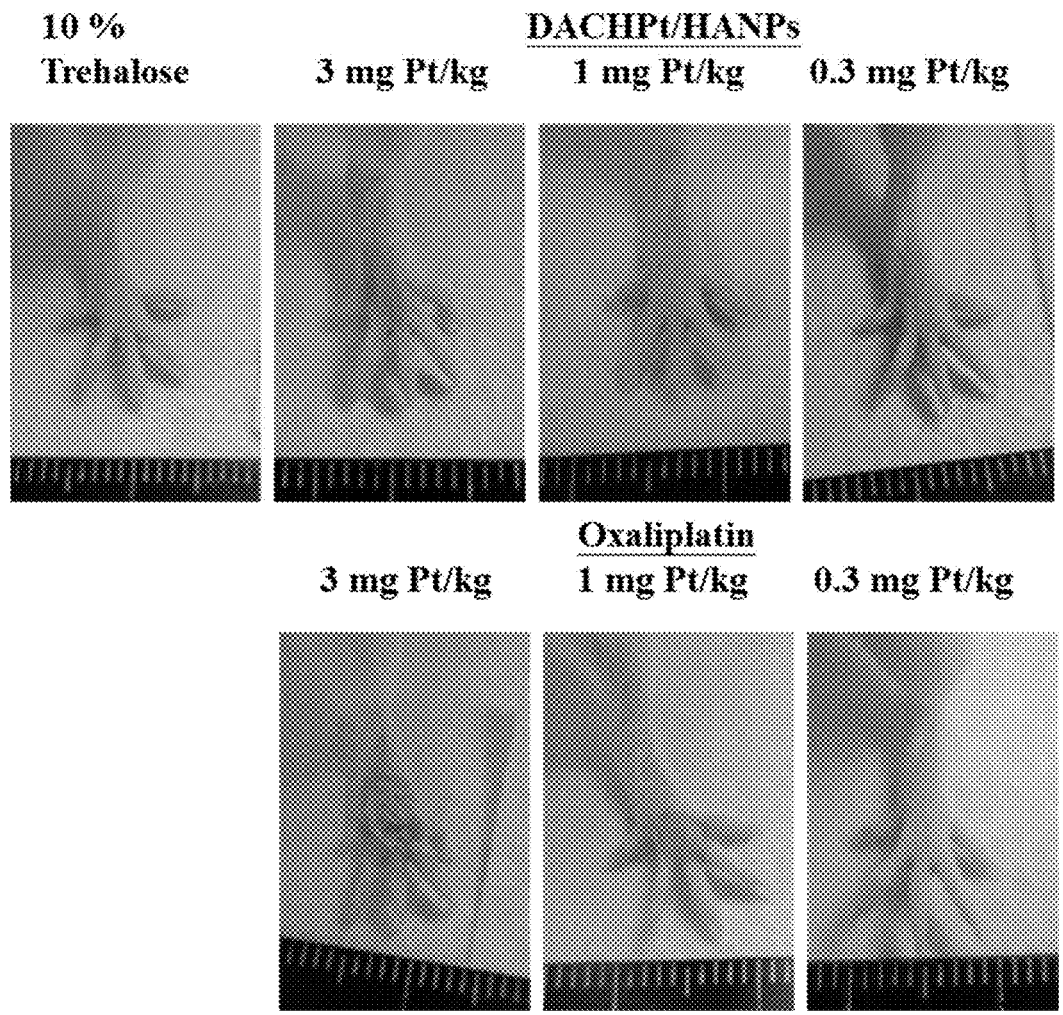
FIG. 11. shows the local skin toxicities of PtHC604 or oxaliplatin by subcutaneously injection.

PDII scoring system showed that skin toxicities was observed in oxaliplatin-treated groups in a dose dependent manner (Table 9 and FIG. 11). Severe skin toxicities were observed at dose of 3 mg Pt/kg of oxaliplatin. Furthermore, PtHC604 at dose of 3 mg Pt/kg showed mild irritation. Lower doses of PtHC604 did not present meaningful local toxicities. PtHC604 was well tolerated in rodents with no signs of injection site morbidity or systemic toxicity. After subcutaneously injection, PtHC604 had lower local toxicities than oxaliplatin. Compared with oxaliplatin, lower local toxicities might be due to lower residual platinum level after PtHC604 treatment.

TABLE 9

Lower local toxicity of PtHC604 over oxaliplatin

| Agent | Dose (mg Pt/kg) | Dermal irritation index | Classification |
|---|---|---|---|
| Oxaliplatin | 3 | 4.8 | Severe irritation |
| | 1 | 0.5 | Mild irritation |
| | 0.3 | 0 | Non-irritation |
| PtHC604 | 3 | 0.5 | Mild irritation |
| | 1 | 0 | Non-irritation |
| | 0.3 | 0 | Non-irritation |

What is claimed is:

1. A method of treating a tumor in a lymphatic system of a subject, comprising:
administering by intravenous injection a hyaluronan nanoparticle comprising a hyaluronic acid derivative and a platinum compound to the subject with tumors in the lymphatic system, wherein the hyaluronic acid derivative comprises:
hyaluronic acid,
modified histidine, and
optionally at least one of a polymer or a $C_4$-$C_{20}$ alkyl,
wherein the modified histidine and the optional at least one of polymer or $C_4$-$C_{20}$ alkyl are grafted at least to primary hydroxyl groups of the hyaluronic acid, and
wherein a graft ratio of the modified histidine is within 20-100%, and a graft ratio of the optional at least one of polymer or $C_4$-$C_{20}$ alkyl is within 0-40% based upon the total number of hydroxyl groups on the hyaluronic acid.

2. The method of claim 1, wherein the hyaluronan nanoparticle comprises a therapeutically effective amount of the platinum compound so as to provide a higher lymphatic AUC compared with intravenous or subcutaneous administration of the platinum compound.

3. The method of claim 1, wherein the platinum compound comprises one or more platinum compound selected from the group consisting of dichloro(1,2-diaminocyclohexane) platinum (DACHPt), cisplatin and oxaliplatin.

4. The method of claim 3, wherein the platinum compound is dichloro(1,2-diaminocyclohexane) platinum (DACHPt).

5. The method of claim 3, wherein the platinum compound is cisplatin.

6. The method of claim 1, wherein the modified histidine is one or more modified histidine selected from the group consisting of Boc-histidine, Cbz-histidine, Fmoc-histidine and Ac-histidine.

7. The method of claim 6, wherein the modified histidine is Boc-histidine, and the graft ratio of the Boc-histidine is within 20-80% based upon the total number of hydroxyl groups of hyaluronic acid.

8. The method of claim 1, wherein the hyaluronic acid comprises the polymer and the polymer is one or more polymer selected from the group consisting of polyethylene glycol (PEG), polycaprolactone (PCL), poly lactic acid (PLA), polyglycolic acid (PGA), poly(lactic-co-glycolic acid)(PLGA) and polyvinylpyrrolidone (PVP).

9. The method of claim 8, wherein the polymer is polyethylene glycol (PEG), and the graft ratio of the polyethylene glycol (PEG) is within 1-40% based upon the total number of hydroxyl groups on the hyaluronic acid.

10. The method of claim 9, wherein the modified histidine is Boc-histidine, the graft ratio of the Boc-histidine is within 20-80% based upon the total number of hydroxyl groups of hyaluronic acid, and the graft ratio of the polyethylene glycol (PEG) is within 1-40% based upon the total number of hydroxyl groups on the hyaluronic acid.

11. The method of claim 10, wherein the graft ratio of Boc-histidine is within 20-80% based upon the total number of hydroxyl groups on the hyaluronic acid and the graft ratio of the polyethylene glycol (PEG) is within 1-20% based upon the total number of hydroxyl groups on the hyaluronic acid.

12. The method of claim 1, wherein the hyaluronic acid comprises the $C_4$-$C_{20}$ alkyl and the $C_4$-$C_{20}$ alkyl is one or more alkyl selected from the group consisting of $C_5H_{11}$, $C_7H_{15}$, $C_9H_{19}$ and $C_{11}H_{23}$.

13. The method of claim 12, wherein the $C_4$-$C_{20}$ alkyl is $C_{11}H_{23}$, and a graft ratio of the $C_{11}H_{23}$ is within 1-40% based upon the total number of hydroxyl groups of hyaluronic acid.

14. The method of claim 13, wherein the modified histidine is Boc-histidine, the graft ratio of the Boc-histidine is within 20-80% based upon the total number of hydroxyl groups on the hyaluronic acid, and the graft ratio of the $C_{11}H_{23}$ is within 1-40% based upon the total number of hydroxyl groups of hyaluronic acid.

15. The method of claim 14, wherein the graft ratio of Boc-histidine is within 20-80% based upon the total number of hydroxyl groups on the hyaluronic acid and the graft ratio of the $C_{11}H_{23}$ is within 1-20% based upon the total number of hydroxyl groups on the hyaluronic acid.

16. The method of claim 1, wherein the modified histidine is Boc-histidine, the hyaluron polymer comprises a polymer comprising polyethylene glycol (PEG), and the platinum compound dichloro(1,2-diaminocyclohexane) platinum (DACHPt).

17. The method of claim 1, wherein the modified histidine is Boc-histidine, the polymer comprises a $C_4$-$C_{20}$ alkyl, and the platinum compound is dichloro(1,2-diaminocyclohexane) platinum (DACHPt).

18. The method of claim 8, wherein the polymer is connected to the hyaluronic acid through linking group(s).

19. The method of claim 12, wherein the polymer is connected to the hyaluronic acid through linking group(s).

20. The method of claim 1, wherein the tumor is metastatic.

21. The method of claim 20, wherein the metastatic tumor is selected from the group consisting of melanoma, head and neck cancer, breast cancer, prostate cancer, lymphoma, gastric cancer, colorectal cancer, ovarian cancer, uterine cancer, and lung cancer.

* * * * *